United States Patent [19]

Victor et al.

[11] Patent Number: 5,161,381
[45] Date of Patent: Nov. 10, 1992

[54] CRYOGENIC LIQUID SAMPLING SYSTEM

[75] Inventors: Richard A. Victor, Grand Island; James D. Augustyniak, Depew, both of N.Y.

[73] Assignee: Praxair Technology, Inc., Danbury, Conn.

[21] Appl. No.: 672,688

[22] Filed: Mar. 20, 1991

[51] Int. Cl.$^5$ .............................................. F25J 3/00
[52] U.S. Cl. ........................................ 62/37; 62/50.1
[58] Field of Search .............. 62/37, 50.1, 50.2, 50.7, 62/515, 511

[56] References Cited

U.S. PATENT DOCUMENTS

| 2,707,868 | 5/1955 | Goodman | 62/511 |
|---|---|---|---|
| 2,750,511 | 6/1956 | Miller | 62/37 |
| 2,764,536 | 9/1956 | Hutchins | 62/37 |
| 2,792,501 | 5/1957 | Barton, Jr. | 62/37 |
| 2,984,988 | 5/1961 | Berger et al. | 62/37 |
| 3,009,864 | 11/1961 | Webb | 62/37 |
| 3,972,202 | 8/1976 | Stearns | 62/51.1 |
| 4,668,261 | 5/1987 | Chatzipetros | 62/37 |

FOREIGN PATENT DOCUMENTS 2107779 8/1972 Fed. Rep. of Germany .

OTHER PUBLICATIONS

Two-Phase Flashing Flow Evaluations, Leung and Nazario, AIChE Apr. 2, 1989.
HTFS Handbook, TP 10 Single Component Two-Phase Choked Flow, pp. 1-4, 1988.
Flow of Fluids, Crane, Technical Paper No. 410 Chapter 2, pp. 8-15.

Primary Examiner—Ronald C. Capossela
Attorney, Agent, or Firm—Stanley Ktorides

[57] ABSTRACT

A sampling system for cryogenic liquid sampling which passes vaporized cryogenic fluid to an analyzer through a conduit having a defined restriction such as an orifice at or downstream of the input and which prevents choke flow in the conduit by simultaneously reducing the pressure which promotes choke flow and improving the ratio of the fluid pressure at and downstream of the restriction in the direction which resists choke flow.

14 Claims, 1 Drawing Sheet

CRYOGENIC LIQUID SAMPLING SYSTEM

TECHNICAL FIELD

This invention pertains to the field of cryogenic liquid sampling for the purpose of composition measurement and is particularly applicable to continuous sampling of cryogenic liquid.

BACKGROUND ART

A cryogenic liquid is a fluid which would be a vapor under ambient conditions of temperature and pressure. Generally a cryogenic liquid is at a temperature of less than 120° K. Typical examples of cryogenic liquids include liquid air, liquid oxygen, liquid nitrogen, liquid argon, liquid methane, liquid helium, liquid neon, liquid krypton, liquid xenon and liquid hydrogen.

Cryogenic liquids are often produced by the cryogenic distillation of a feed such as air in a cryogenic distillation plant comprising one or more cryogenic distillation columns. In order to ensure that the plant is operating properly and also to ensure that product of the requisite purity is being produced, it is necessary to obtain samples of cryogenic liquid from a column and to analyze the sample.

After they are produced, cryogenic liquids are transported from the production facility to the use site, generally in cylinders or tanker trucks, and may be stored at the use site in storage tanks. In order to ensure that the cryogenic liquid has not been contaminated in transportation and/or storage, it is necessary to have a sample of the cryogenic liquid analyzed for contaminants.

One method of sampling cryogenic liquid is the batch technique wherein a sample of cryogenic liquid is caused to flow into a capture device. The flow of cryogenic liquid is then shut off and the sample is warmed to produce a gas which is passed on to one or more analyzers. In the process a large amount of the sample is vented and lost. The batch method is disadvantageous for several reasons. First, as mentioned, a large amount of the sample is vented and thus lost. Second the batch capture system is complicated and costly. Third, and perhaps most important, the batch technique is inherently limited in timeliness of the information obtained.

Another method for sampling cryogenic liquid which enables a continuous sampling of the cryogenic liquid is the coupling of an analyzer system to a cryogenic liquid source though a conduit which is sufficiently long so as to enable the cryogenic liquid to vaporize prior to reaching the analyzer or analyzers. Two major problems arise with this method. First the vaporization of the cryogenic liquid in the conduit results in choke flow conditions which cause local pressure increases causing liquid to flow back out of the conduit and into the cryogenic liquid source. This is undesirable and, particularly in the case where the source is a distillation column, will cause an inaccuracy in the reading due to rectification of the sample. In a multicomponent sample such as one containing nitrogen, argon and oxygen the back flowing vapor will be concentrated in the lowest boiling component, which in this case is nitrogen, and the back flow of vapor against countercurrently flowing liquid causes further distillation of the sample which in this case concentrates the highest boiling component oxygen in the liquid.

Another problem with the known continuous method is that the requisite long conduit affords an opportunity for a significant amount of trace impurities within the sample to plate onto the inside surface of the conduit. Plating is the solidification or condensation of constituents from the cryogenic fluid sample onto the conduit inner surface. Examples include the plating of high boiling carbon dioxide, water vapor or methane from a liquid oxygen sample onto the conduit inner walls.

Still further, the requisite long conduit results in a long response time from the taking of the sample to the making of the analysis.

Accordingly it is an object of this invention to provide an improved system for taking and analyzing a cryogenic liquid sample.

It is another object of this invention to provide an improved system for sampling and analyzing a cryogenic liquid on a continuous basis.

SUMMARY OF THE INVENTION

The above and other objects which will become apparent to one skilled in the art upon a reading of this disclosure are attained by the present invention one aspect of which is:

Apparatus for sampling a cryogenic liquid comprising:

(A) a source of cryogenic liquid;

(B) conduit means communicating with the source of cryogenic liquid and having a restriction at or downstream of the point where cryogenic liquid flows into the conduit; and (C) analyzer means in flow communication with said conduit downstream of the restriction.

Another aspect of this invention is:

Method for sampling a cryogenic liquid comprising:

(A) passing cryogenic liquid into a conduit having a restriction so that the cryogenic fluid flows in the conduit past the restriction at a mass flowrate less than the choke flowrate;

(B) vaporizing cryogenic liquid within the conduit downstream of the restriction; and (C) passing resulting vapor out of the conduit into an analyzer at a rate sufficient to maintain the pressure within the conduit lower than the head pressure at or upstream of the restriction and preventing back flow within the conduit.

As used herein the term "fluid flow cross sectional area" means the area at a given point in a conduit through which fluid may flow. For a conduit with a circular cross section the fluid flow cross sectional area would be the area at a point calculated using the inside diameter of the conduit at that point.

As used herein the term "choke flow" means the maximum mass discharge rate of a fluid through a conduit with respect to a given head pressure such that the mass discharge rate cannot be further increased by reducing the downstream pressure.

As used herein the term "head pressure" means the total pressure at the inlet of a conduit and represents the sum of the pressure head, velocity head and elevation head.

As used herein the term "choke flowrate" means the mass flowrate which occurs at choke flow conditions.

As used herein the term "analyzer" means a device used for measurement of the gas composition of a fluid mixture.

DETAILED DESCRIPTION

The invention comprises a system whereby vaporized cryogenic liquid may be provided to an analyzer or a plurality of analyzers at a mass flowrate below the choke flowrate so as to avoid choke flow. In a preferred embodiment the invention further avoids plating prior to the analyzer. The invention comprises a defined restriction at or downstream of the input end of the conduit connecting the source of cryogenic liquid to the analyzer. The restriction simultaneously produces two complementary fluid dynamic effects. First, the restriction limits the mass of cryogenic fluid flowing past the restriction to a rate below the choke flowrate thus limiting the amount of fluid which can vaporize to create back pressure within the conduit. Second the restriction, through its pressure drop helps mitigate the choke flow conditions within the conduit downstream of the restriction.

Figure 1:
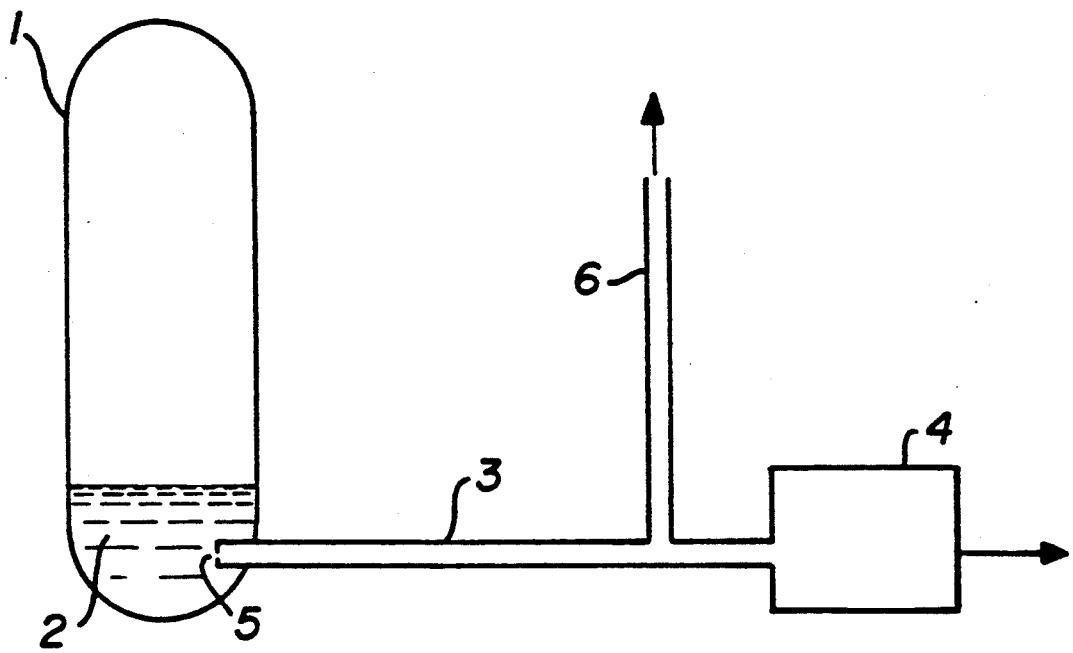
FIG. 1 is a simplified cross sectional representation of one preferred embodiment of the system of this invention wherein the restriction is an orifice at the point where cryogenic liquid flows into the conduit.

The invention will be described in greater detail with reference to the drawings which illustrate an orifice at the inlet of the conduit as the restriction. Instead of an orifice the restriction could comprise, for example, a venturi, a valve or a capillary tube. Referring now to FIG. 1 there is illustrated a source 1 of cryogenic liquid 2 which in this case is a simplified representation of a distillation column. Conduit 3 communicates with the source of cryogenic liquid and with analyzer 4 which may be any suitable analyzer such as an infrared carbon dioxide analyzer, a paramagnetic oxygen analyzer or an electrochemical oxygen analyzer. If desired, a plurality of analyzers may be employed by, for example, splitting conduit 3 into a plurality of branches each leading to an analyzer or by passing the fluid from conduit 3 into a series of sample vessels each of which communicates with an analyzer. Conduit 3 may have any suitable geometry. However, it is preferred that conduit 3 be cylindrical wherein its radical cross section or fluid flow cross sectional area is a circle.

Figure 2:
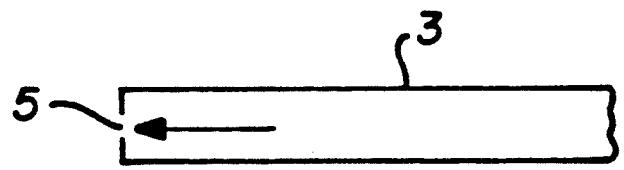
FIG. 2 is an enlarged cross sectional representation of the orifice useful in the practice of this invention as shown in FIG. 1.

At the point where the cryogenic liquid flows into conduit 3 there is an orifice 5 having a fluid flow cross sectional area not exceeding 55 percent, and preferably not exceeding 10 percent, of the fluid flow cross sectional area of the conduit. FIG. 2 is an enlarged representation of the portion of FIG. 1 showing the orifice, and the numerals in FIG. 2 correspond to those of FIG. 1. The constriction established by the restriction such as an orifice, mitigates the pressure condition of the cryogenic fluid which counteracts the tendency toward the establishment of choke flow conditions within the downstream conduit. In addition the defined orifice simultaneously reduces the pressure promoting choke flow by reducing the mass flowrate of cryogenic liquid into the conduit. This mass flowrate reduction reduces the amount of liquid vaporized downstream in the conduit and thus reduces the amount of vapor formed and the consequent back pressure generated. When the restriction is in the form of a venturi, short capillary tube or a valve, the restriction should have a geometry such that fluid flow through the restriction experiences a pressure drop and mass flowrate comparable or equivalent to that experienced by flow passing through an orifice having a fluid flow cross sectional area not exceeding 55 percent of the fluid flow cross sectional area of the conduit.

As the cryogenic liquid passes through conduit 3 it is vaporized by heat transfer through the conduit walls by ambient heat and is then passed on to the analyzer(s) as previously discussed at a rate which maintains the pressure within the conduit lower than the pressure at the orifice so as to avoid back flow. If desired a vent 6 may be put onto conduit 3 to increase the gas flowrate which improves the sample transfer response time.

In a preferred embodiment of the invention conduit 3 has a fluid flow cross sectional area not exceeding 1 square inch and preferably not exceeding 0.03 square inch. This defined small fluid flow cross sectional area, which is especially useful for applications involving measurement of trace constituents, causes the fluid passing through the conduit to pass at a high velocity of at least 150 feet per second (fps) and preferably of at least 170 fps. Generally the velocity of the fluid passing through the conduit will have a velocity within the range of from 150 to 200 fps. This high velocity overcomes the inaccuracies heretofore experienced with known systems due to plating of trace impurities onto the conduit surface. As can be appreciated, when only a trace amount of impurity is present, the plating of even a small amount will result in a significant percentage error in the analyzer reading from the actual concentration present in the cryogenic liquid.

The defined high velocity of the cryogenic fluid counteracts plating by two mechanisms. First the increased velocity reduces the residence time required for fluid to traverse the conduit thus providing a reduced opportunity for solidification and/or condensation onto the conduit inner surface. Second any such solidified or condensed matter is quickly swept back into the fluid flow by the higher velocity of the fluid flowing through the conduit thus preventing the deleterious buildup of matter on the conduit inner surface which, under conventional conditions, would further promote solidification and/or condensation. In addition, the high velocity leads to a reduced response time further increasing the utility of the invention. The faster response time is particularly advantageous in conjunction with continuous monitoring, i.e. sampling and analysis, of the cryogenic liquid. Continuous monitoring is particularly useful when monitoring the operation of a distillation column.

The invention may be effectively employed to sample cryogenic liquid on a batch or continuous basis but will find its greatest utility with continuous analysis. It may be used to sample cryogenic liquid from a storage tank at a use site, from a transport vessel such as a cylinder, or from any other source of cryogenic liquid. One particularly useful application of the invention is continuous sampling of cryogenic liquid from a distillation column enabling the operation to monitor a cryogenic distillation plant with effective real time data. In the case of the monitoring of a cryogenic liquid from a distillation column, typical compositional measurements involve essentially bulk constituents and hence a very high velocity, on the order of 170 fps, is not required. However, in order to achieve adequate response times, velocities may approach or exceed this value. For example, knowing the lower column kettle liquid composition of a double column plant enables one to calculate the shelf flow rate by a oxygen balance thus setting both the lower and upper column reflux rates. This sets the operating and equilibrium lines and allows one to easily evaluate the lower column theoretical stages.

One skilled in the art will recognize that it is the unique properties of cryogenic liquids which work in concert with the system of the invention to enable the attainment of the beneficial results. Although the invention has be described in detail with reference to certain preferred embodiments, those skilled in the art will recognize that there are other embodiments of the invention within the spirit and scope of the claims.

We claim:

1. Apparatus for sampling a cryogenic liquid comprising:
   (A) a source of cryogenic liquid;
   (B) conduit means having a fluid flow cross sectional area not exceeding 0.03 square inch communicating with the source of cryogenic liquid and having a restriction at the point where the source of cryogenic liquid communicates with the conduit; and
   (C) analyzer means in flow communication with said conduit downstream of the restriction, said restriction limiting the mass of cryogenic liquid flowing past the restriction to a rate below the choke flowrate while all liquid flowing past the restriction is vaporized before reaching the analyzer.

2. The apparatus of claim 1 wherein the restriction comprises an orifice having a fluid flow cross sectional area not exceeding 55 percent of the fluid flow cross sectional area of the conduit.

3. The apparatus of claim 2 wherein the orifice has a fluid flow cross sectional area not exceeding 10 percent of the fluid flow cross sectional area of the conduit.

4. The apparatus of claim 1 wherein the conduit has a fluid flow cross sectional area not exceeding 1 square inch.

5. The apparatus of claim 1 wherein the conduit is cylindrical.

6. The apparatus of claim 1 wherein the source of cryogenic liquid is a distillation column.

7. The apparatus of claim 1 further comprising vent means on the conduit downstream of the restriction and upstream of the analyzer.

8. Method for sampling a cryogenic liquid comprising:
   (A) passing cryogenic liquid from a source of cryogenic liquid into a conduit having a restriction at the point where the source of cryogenic liquid communicates with the conduit so that the cryogenic fluid flows in the conduit past the restriction at a mass flowrate less than the choke flowrate and at a velocity which is at least 150 feet per second;
   (B) vaporizing all the cryogenic liquid which flows past the restriction within the conduit downstream of the restriction; and
   (C) passing vapor resulting from step (B) out of the conduit into an analyzer at a rate sufficient to maintain the pressure within the conduit lower than the head pressure at or upstream of the restriction and preventing back flow within the conduit.

9. The method of claim 8 wherein the restriction comprises an orifice having a fluid flow cross sectional area not exceeding 55 percent of the fluid flow cross sectional area of the conduit.

10. The method of claim 9 wherein the orifice has a fluid flow cross sectional area not exceeding 10 percent of the fluid flow cross sectional area of the conduit.

11. The method of claim 8 wherein the cryogenic fluid passes through the conduit at a velocity which is at least 170 feet per second.

12. The method of claim 8 wherein the cryogenic liquid comprises liquid oxygen.

13. The method of claim 8 wherein the cryogenic liquid comprises liquid nitrogen.

14. The method of claim 8 wherein the cryogenic liquid comprises at least one liquid from the group consisting of liquid argon, liquid methane, liquid helium, liquid neon, liquid krypton, liquid xenon and liquid hydrogen.

* * * * *